United States Patent [19]

Daniel et al.

[11] 4,271,055

[45] Jun. 2, 1981

[54] PROCESS FOR PREPARING AN AQUEOUS LATEX BINDER FOR MANUFACTURING NONWOVENS EMPLOYING ULTRAFILTRATION TO FORM A LATEX HAVING LOW HYDROSOLUBLES

[75] Inventors: Jean-Claude Daniel, Fontenay-sous-Bois; Jacques Grossoleil, Paris; Robert Roullet, Lyons, all of France

[73] Assignee: Rhone-Poulenc Industries, Paris, France

[21] Appl. No.: 898,954

[22] Filed: Apr. 21, 1978

[30] Foreign Application Priority Data

Apr. 22, 1977 [FR] France ................. 77 12161

[51] Int. Cl.³ .................. D04H 1/64; C08F 6/16
[52] U.S. Cl. .................. 260/29.6 TA; 260/29.6 PT; 260/29.7 H; 260/29.7 PT; 260/34.2; 428/290; 528/499; 528/502
[58] Field of Search ............... 260/29.6 PT, 29.7 PT, 260/29.7 H, 29.6 TA; 528/499, 502

[56] References Cited

U.S. PATENT DOCUMENTS

| | | | |
|---|---|---|---|
| 3,046,259 | 7/1962 | Hess et al. | 528/502 |
| 3,052,663 | 9/1962 | Bodlaender et al. | 528/499 |
| 3,248,455 | 4/1966 | Harsch et al. | 528/499 |
| 3,345,430 | 10/1967 | Simon et al. | 528/499 |
| 3,371,059 | 2/1968 | Rich | 260/29.6 PT |
| 3,505,263 | 4/1970 | Roth | 260/29.7 R |
| 3,511,799 | 5/1970 | Clampitt | 260/29.6 PT |
| 3,526,098 | 9/1970 | Huhn et al. | 62/68 |
| 3,531,448 | 9/1970 | Johnson | 528/502 |
| 3,701,764 | 10/1972 | Hargitay | 260/29.6 PT |
| 3,930,931 | 1/1976 | Baughman | 159/4 ST |
| 3,944,513 | 3/1976 | Greenwald et al. | 260/29.6 PT |
| 4,086,413 | 4/1978 | Stedefeder et al. | 260/29.6 PT |

FOREIGN PATENT DOCUMENTS

| | | | |
|---|---|---|---|
| 1131013 | 6/1962 | Fed. Rep. of Germany | 260/29.6 PT |
| 935036 | 8/1963 | United Kingdom | 260/29.6 PT |

*Primary Examiner*—Joseph L. Schofer
*Assistant Examiner*—Herbert J. Lilling
*Attorney, Agent, or Firm*—McDougall, Hersh & Scott

[57] ABSTRACT

Aqueous latex base binder of a synthetic polymer for manufacturing nonwoven fabrics, and specifically webs for sanitary use having improved breaking strength. The content in the latex of hydrosoluble compounds dissolved in the aqueous phase is less than 0.5% by weight in relation to the polymer.

3 Claims, 1 Drawing Figure

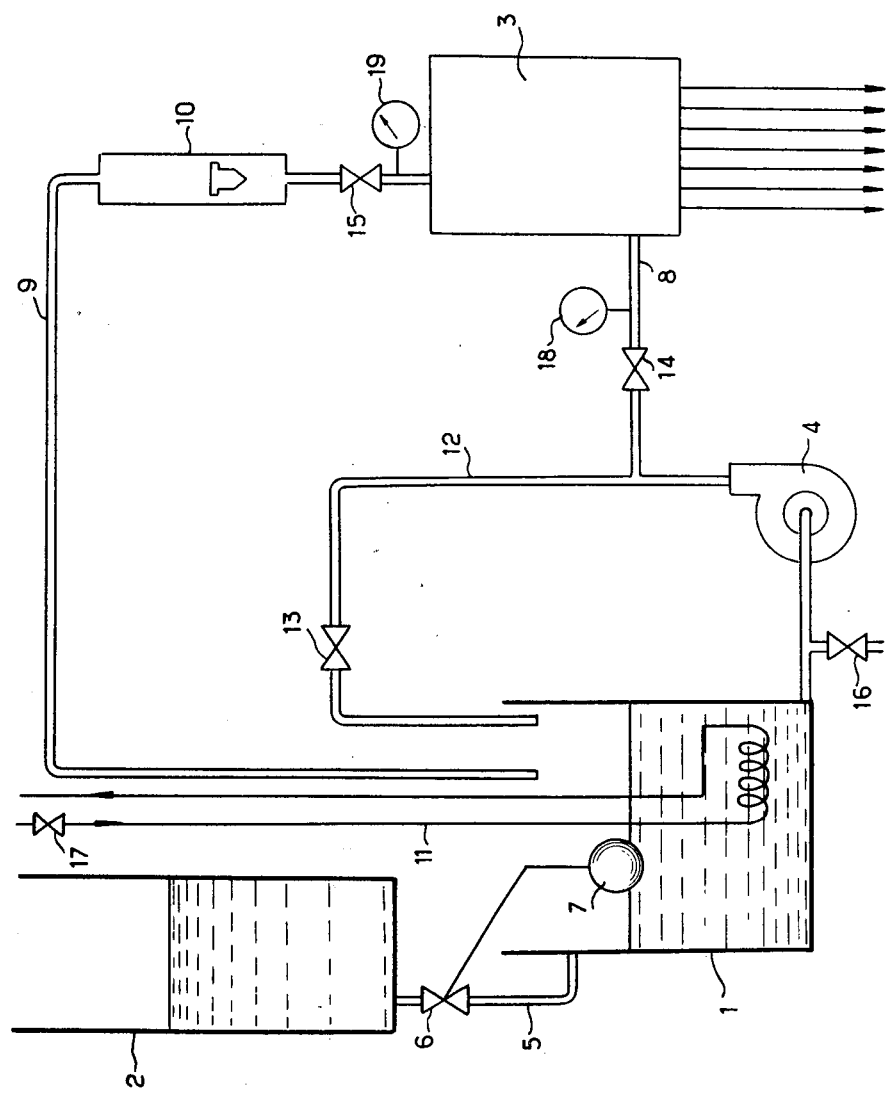

PROCESS FOR PREPARING AN AQUEOUS LATEX BINDER FOR MANUFACTURING NONWOVENS EMPLOYING ULTRAFILTRATION TO FORM A LATEX HAVING LOW HYDROSOLUBLES

This invention relates to an aqueous latex base binder of a synthetic polymer for manufacturing nonwoven fabrics, especially webs for sanitary use. It also pertains to the nonwoven fabrics manufactured with the aforementioned binder.

Nonreusable sanitary nonwoven fabrics, such as liners for diapers, sanitary napkins, bandages, etc., are obtained from webs prepared by dry and wet processes. In most cases, the actual binding operation entails only partial binding carried out on one of the surfaces of the nonwoven fabric, carried out according to a classical pressing process or according to any of the other known techniques (binding by mass precipitation, pulverization, saturation, etc.).

In most cases, the bath used during the binding operation consists of a latex base binder and a thickener for controlling viscosity of the bath and, hence, the weight of the deposit, possibly a surface-active agent and possibly an antifoaming agent. The bonded web is then dried in a furnace. Carboxymethyl celluloses or their derivatives, sodium polyacrylates or aqueous emulsions of polyacrylic acids are generally used as thickeners.

The main characteristics required of nonwoven fabrics after binding are breaking strength, especially in a wet medium, elasticity which determines the quality of contact with the skin, and high thermobonding capacity.

The binders, according to the invention, embody an aqueous latex base of a synthetic polymer with a content of hydrosoluble compounds dissolved in the aqueous phase of less than 0.5% by weight in relation to the polymer.

The hydrosoluble compounds primarily include salts formed, for example, by catalytic residues, surface-active agents and macromolecular compounds such as carboxyl compounds.

The applicant has found that, all things being equal in other respects, a latex with a sufficiently low content of hydrosoluble compounds dissolved in the aqueous phase produces nonwoven fabrics with improved breaking strength.

The following can be cited as synthetic polymers usable as latexes according to the invention: styrene-butadiene copolymers, carboxylated styrene-butadiene copolymers, alkyl acrylate-vinyl chloride copolymers, carboxyl alkyl acrylate-vinyl chloride copolymers, vinylidene chloride-vinyl chloride copolymers, carboxyl vinylidene chloride-vinyl chloride copolymers, alkyl polyacrylates and carboxyl alkyl polyacrylates.

The content in the latex of hydrosoluble compounds dissolved in the aqueous phase can be estimated by using the method hereinafter described in which semi-permeable membranes with high cutoff are used to let low-molecular-weight compounds flow through and, if need be, carboxyl macromolecular compounds, while blocking passage of polymer particles.

The latex to be tested, having a ponderal dry material content $t_1$, expressed in percent by weight, undergoes ultrafiltration by passing through a laboratory ultrafiltration module equipped with a semi-permeable membrane, as marketed by Rhone-Poulenc Industries in France under the tradename: "Iris 3538". The ponderal dry material content is determined from the first drop of permeate collected $t_p$, expressed in percent by weight, which equals that of the aqueous phase of the latex.

The content in the latex of hydrosoluble compounds dissolved in aqueous phase $t_s$, expressed in percent by weight in relation to the polymer, is determined by the formula:

$$t_s = \frac{t_p(100 - t_1)}{t_1}$$

A latex usable as a binder according to the invention is usually obtained from a latex of a synthetic polymer which is known to be usable for impregnating nonwoven webs and which is prepared by any known aqueous emulsion polymerization process, and by eliminating from the latter a sufficient quantity of the aforementioned hydrosoluble compounds. These can be eliminated, for example, by ultrafiltration through a semipermeable membrane. As ultrafiltration progresses, the compounds dissolved in the aqueous phase flow through the membrane in the permeate while the hydrosoluble compounds adsorbed at the surface of the latex particles are progressively desorbed and eliminated. The ultrafiltration operation can be carried out in a classical unit of a type commonly employed in industry.

A cross-section of this type of unit is shown in the attached FIGURE.

Basically, it consists of tank 1 containing the latex to be processed, tank 2 containing deionized water, ultrafilter 3 and pump 4. Tank 1 is fed by tank 2 which supplies deionized water through pipe 5; and automatic valve 6, actuated by float 7, maintains constant the level of the bath contained in tank 1. Pump 4 ensures latex flow through pipe 8 toward ultrafilter 3. Through pipe 9, on which flowmeter 10 is fitted, the concentrate delivered by ultrafilter 3 is recycled into tank 1. Heat exchange fluid circulates through coil 11 immersed in the latex contained in tank 1 to maintain it at a constant temperature. Pipe 12 is used to put the unit in stable working condition.

The unit is also equipped with shutoff valves 13, 14, 15, 16 and 17 and manometers 18 and 19.

The maintenance of stable working conditions and the operation proceed as follows: with valve 14 closed and valve 13 open, pump 4 is turned on; then valves 14 and 15 are opened and valve 13 closed. By successive approximations, the opening of valves 14 and 15 is regulated so as to obtain the desired flow of latex at the desired pressure, the pressure differences indicated by manometers 18 and 19, representing the pressure drop in ultrafilter 3.

To ensure good operation of the ultrafiltration technique, it is advantageous in accordance with the practice of this invention to respect the following conditions:

The semi-permeable membrane should have a high cutoff, generally between 5000 and 100000, expressed as the molecular-weight-value of standard proteins in a neutral, buffered medium.

The flow rate of the latex on the membrane should be higher than 0.5 m/s (meters per second) and preferably between 1 and 2 m/s, to prevent the membrane from clogging. At the same time, it also limits the pressure drop in the ultrafilter and the shearing which the latex undergoes.

The pressure differences on each side of the membrane should be between 0.1 and 6 bars, and preferably between 1.5 and 3 bars.

The temperature of the latex should be between 0° and 100° C., and preferably between 0° and 50° C.

Since the flow rate of the permeate decreases as the ponderal dry material content of the latex increases, it is preferable to accomplish ultrafiltration with a perceptibly constant ponderal content, generally between 5 and 70%, and preferably between 45 and 55%, possibly after dilution, especially if the latex viscosity is very high.

Unit shutdown should be followed by an adequate cleaning cycle with pure water to prevent irreversible clogging, hence destroying the membrane.

If the mechanical stability of the latex is insufficient to permit ultrafiltration without forming agglomerates, one can proceed by first bringing the latex to an alkaline pH value of usually between 7.5 and 9.5. After ultrafiltration is completed, the latex can be concentrated, if need be, until its dry material content is suitable for the intended usage.

The following examples are provided to illustrate the invention.

EXAMPLES 1-4

Examples 1 and 3 are given for comparative purposes. Examples 2 and 4 illustrate the invention.

Partial binding is carried out on one side of a 1.5 denier, 40 mm long viscose carded web. The carded web is dipped in the binding bath, then compressed between two cylinders to ensure penetration of the binder into the web. The web is then dried in a tunnel furnace at 150° C. for 2 minutes.

The treated web is tested for breaking strength, stiffness and thermobonding capacity by means of the following methods:

Breaking Strength:

This is determined with a dynamometer known in industry as a "Lhomargy". The measurement requirements are as follows:

| Test tube sizes | 5 × 20 cm |
|---|---|
| Traction speed | 10 cm/mn |
| Initial distance between jaws | 15 cm |

Measurements are taken lengthwise and crosswise. They are taken when dry. They are also taken when wet, i.e., after the test tubes have been immersed in water at 37° C. for 15 minutes.

"Cantilever" Stiffness:

This is determined according to standard ASTM D 1388. Measurements are taken lengthwise and crosswise.

Thermobonding Capacity:

This is determined with a "Lhomargy" dynamometer, by measuring the tearing-resistance of two bonded samples of nonwoven webs which have been bonded between two moving jaws heated to 150° C. and rotating at 100 tr/mn. The measurement requirements are as follows:

| Test tube width | 5 cm |
|---|---|
| Traction speed | 10 cm/mm |

Two samples bonded on their coated side and two samples bonded on their noncoated side are measured.

The following table gives, for each example, the reference of the aqueous latexes used as binders, the nature of the polymer of which they are composed and their content by weight of hydrosoluble compounds dissolved in the aqueous phase in relation to the polymer.

TABLE 1

| | Reference | Nature of Polymer | Hydrosoluble compound content by weight in relation to the polymer (%) |
|---|---|---|---|
| Example 1 | A | Carboxyl butyl acrylate-vinyl chloride copolymer composed of, by weight, 39% vinyl chloride, 59% butyl acrylate and 2% ethylene carboxylic acid | 2.25 |
| Example 2 | B | Carboxyl butyl acrylate-vinyl chloride copolymer composed of, by weight, 39% vinyl chloride, 59% butyl acrylate and 2% ethylene carboxylic acid | 0.25 |
| Example 3 | C | Carboxyl styrene-butadiene copolymer composed of, by weight, 43% butadiene, 53% styrene and 4% ethylene carboxylic acids | 4.7 |
| Example 4 | D | Carboxylic styrene-butadiene copolymer composed of, by weight, 43% butadiene, 53% styrene and 4% ethylene carboxylic acids | 0.3 |

Latexes B and D, used in the examples illustrating the invention, were obtained from latex A with 55% dry material content by weight and latex C with 50% dry material content by weight, respectively, these being used in the comparative examples, the latter undergoing ultrafiltration as hereinafter explained. Before undergoing this process, the latex in Example 2 is brought to a ponderal dry material content of 50% by adding deionized water, whereas the latex in Example 4 remains as is.

Ultrafiltration is carried out in a unit with an ultrafiltration surface area of 0.7 m². The unit is equipped with a membrane with a cutoff of 20000, which is marketed by Rhone-Poulenc Industries in France under the tradename "Iris 3538", and is fed by a pump capable of supplying 6 m³/h at a pressure of 3 bars. During ultrafiltration, the dry material content in the latex is maintained constant with deionized water.

Table 2 shows the ultrafiltration time for each example, according to the invention.

TABLE 2

| | Ultrafiltration Time (hours) |
|---|---|
| Example 2 | 9 |
| Example 4 | 12 |

When ultrafiltration is completed, latex B is concentrated to its initial dry material content of 55% by weight. After drainage, the unit is flushed clean with water. No clogging of the membrane is noticed.

Latexes A, B, C and D are diluted with deionized water to a dry material content of 40% by weight, then sodium polyacrylate is added until their viscosity reaches approximately 1000 centipoises.

Table 3 below shows the results obtained for each example. It also indicates the weight of the nonwoven web and the weight of the binder deposited.

TABLE 3

|  | Example 1 | Example 2 | Example 3 | Example 4 |
| --- | --- | --- | --- | --- |
| Weight of nonwoven web (g/m2) | 16.4±0.6 | 15.8±0.5 | 17±1 | 18.0±0.5 |
| Weight of binder deposited (g/m2) | 4.2 | 3.9 | 4.5 | 4.5 |
| Breaking strength (g/5cm) | | | | |
| - lengthwise | | | | |
| . when dry | 3000±120 | 3100±200 | 3180±200 | 3350±300 |
| . when wet | 1100±70 | 1180±70 | 1300±100 | 1500±60 |
| - crosswise | | | | |
| . when dry | 375±30 | 435±50 | 485±50 | 520±65 |
| . when wet | 85±10 | 125±10 | 95±5 | 140±10 |
| "Cantilever" Stiffness (mg/cm) | | | | |
| - lengthwise | 56±2 | 56±2 | 80±5 | 80±5 |
| - crosswise | 7±1 | 7±1 | 9±1 | 9±1 |
| Thermobonding capacity (g/5cm) | | | | |
| - coated sides | 190±15 | 195±15 | 220±15 | 230±15 |
| - noncoated sides | 245±20 | 260±20 | 275±20 | 280±20 |

It will be seen that latexes B and D, used as binders in the invention, yield webs displaying better breaking strength, especially in a wet medium, than those bonded with latexes A and C.

We claim:

1. Process for preparing an aqueous latex base binder of a synthetic polymer in which the content in the latex of hydrosoluble compounds is less than 0.5% by weight in relation to the polymer, comprising subjecting a latex formed by aqueous emulsion polymerization to ultrafiltration, through a semi-permeable membrane, to remove a quantity of the hydrosoluble compounds, adding water to maintain the ponderal content of dry material in the latex within the range of 5–70% by weight.

2. Process as claimed in claim 1, in which ultrafiltration is carried out with a perceptibly constant ponderal latex content in dry material.

3. The process as claimed in claim 1, in which the ponderal weight of dry material in the latex is maintained within the range of 45–55% by weight.

* * * * *